United States Patent [19]

Diamond et al.

[11] 4,008,269

[45] * Feb. 15, 1977

[54] PHENYLACETIC ACIDS

[75] Inventors: Julius Diamond, Lafayette Hill; Norman Julian Santora, Roslyn, both of Pa.

[73] Assignee: William H. Rorer, Inc., Fort Washington, Pa.

[ * ] Notice: The portion of the term of this patent subsequent to Dec. 3, 1991, has been disclaimed.

[22] Filed: Dec. 10, 1973

[21] Appl. No.: 423,444

Related U.S. Application Data

[60] Division of Ser. No. 152,387, June 11, 1971, which is a continuation-in-part of Ser. Nos. 34,870, May 5, 1970, Pat. No. 3,864,384, and Ser. No. 152,387, June 11, 1971, Pat. No. 3,852,323.

[52] U.S. Cl. .................... 260/515 A; 260/268 R; 260/284; 260/286 R; 260/293.72; 260/293.8; 260/293.81; 260/293.83; 260/293.84; 260/295 S; 260/448 R; 260/469; 260/471 R; 260/473 R; 260/473 S; 260/501.16; 260/520 R

[51] Int. Cl.$^2$ ................ C07C 63/33; C07C 69/76
[58] Field of Search .............. 260/515 A, 469, 520, 260/473 R, 473 S, 479 R, 501.16, 295 S, 268 R, 293.72, 293.8, 293.81, 293.83, 293.84, 286 R, 284, 448 R

[56] References Cited

UNITED STATES PATENTS

| | | | |
|---|---|---|---|
| 2,953,565 | 9/1960 | Faust et al. | 260/515 A |
| 3,864,384 | 5/1970 | Diamond et al. | 260/469 |

*Primary Examiner*—Jane S. Myers
*Attorney, Agent, or Firm*—Erich M. H. Radde

[57] ABSTRACT

Novel α-halo-p-cycloalkylphenylacetic acids and their derivatives have been prepared. Compounds of this invention possess useful anti-inflammatory, analgesic and antipyretic properties.

9 Claims, No Drawings

PHENYLACETIC ACIDS

CROSS REFERENCES TO RELATED APPLICATIONS

This is a division, of application Ser. No. 152,387, filed June 11, 1971, which is a continuation-in-part application of Ser. No. 34,870 filed May 5, 1970, now U.S. Pat. No. 3,864,384, and Application Ser. No. 152,387, filed June 11, 1971, is now U.S. Pat. No. 3,852,323.

SUMMARY OF THE INVENTION

This invention describes certain α-halo-p-cycloalkylphenylacetic acids and their derivatives and their use in therapeutic compositions. In addition, this invention relates to the preparation of these α-halo-p-cycloalkylphenylacetic acids. When the compounds of this invention are administered to mammals, they afford significant treatment of inflammation and associated pain and fever.

They further provide analgesic and antipyretic methods for the relief and treatment of pain and fever associated with inflammation.

BACKGROUND OF THE INVENTION

There has been continued efforts in research to develop drugs which would significantly inhibit the development of inflammation and relieve the pain and fever associated with it. Much of these efforts have been carried on in the field of steroids. While many of these compounds have been effective, they have had the drawback of causing many side effects.

We have unexpectedly found that α-halo-p-cycloalkylphenylacetic acid compounds and their derivatives have valuable pharmacologic properties.

We have found that α-halo-p-cycloalkylphenylacetic acid compounds and their derivatives possess useful anti-inflammatory, analgesic and antipyretic properties.

We have also found a series of anti-inflammatory compounds which are non-steroidal.

We have further found that these α-halo-p-cycloalkylphenylacetic acid compounds and their derivatives are novel.

We have also found that the compounds of this invention are useful in effectively providing a method for the inhibition of inflammation and the treatment of associated pain and fever.

We have still further found an entirely new class of anti-inflammatory, analgesic and antipyretic pharmaceutical compositions containing the α-halo-p-cycloalkylphenylacetic acids and derivatives of this invention as active ingredient.

We have again found a convenient method for synthesizing these compounds.

DESCRIPTION AND PREFERRED EMBODIMENT

This invention comprises a class of novel chemical compounds which contain a cycloalkyl radical which is attached to a substituted phenyl-α-haloacetic acid in the para-position. This invention further comprises derivatives of said acetic acids and the method of preparing the same.

This invention also describes a new method of treating inflammation and associated pain and fever as well as novel therapeutic compositions.

The compounds of this invention can be represented by the generic structure which is described by the general formula I

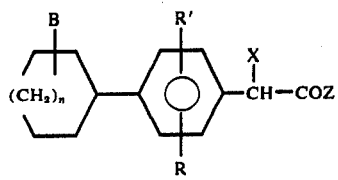

where:
n is
  0–2;
B is
  hydrogen or
  loweralkyl;
R is
  hydroxy,
  loweralkoxy,
  acyloxy,
  acetyl or
  loweralkyl;
R' is
  hydrogen,
  fluoro,
  chloro,
  bromo,
  trifluoromethyl or,
  nitro;
X is
  halo;
Z is
  —OH,
  loweralkoxy,
  arloweralkoxy, or
  —OM (where M is an alkali, alkaline earth or aluminum metal or an ammonium salt).

The compounds of this invention contain an asymmetric carbon atom in the alpha-position of the acetic acid side chain. As a result, the above compounds of formula I may be obtained as racemic mixtures of their dextro (+) and levorotatory (−) isomers. It is to be understood that said $d$ and $l$ isomers as well as the dl mixtures thereof are embraced within the scope of this invention.

When B is loweralkyl, two racemic mixtures may exist in the case of 2'- or 3'-loweralkylcyclohexylphenyl-α-haloacetate, 2'- or 3'-loweralkylcyclopentylphenyl-α-haloacetate, 2'- or 3'- or 4'-loweralkylcycloheptylphenyl-α-haloacetate or their derivatives. It is understood that both racemic mixtures are embraced within the scope of this invention.

The preferred R and R' substituents are in the 3 and 5 positions.

The preferred compounds of this embodiment describe the cyclohexyl class of chemical compounds which have particular usefulness as anti-inflammatory, analgesic and antipyretic agents. These compounds are described in formula II

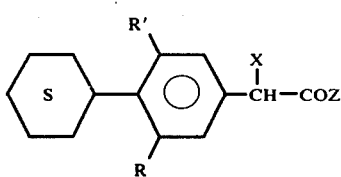

where:
R, R', X and Z are as described above.

Those compounds whose properties are even more preferred are also described by formula II
where:
R is
 hydroxyl,
 loweralkoxy,
 acetyloxy,
 acetyl, or
 loweralkyl;
R' is
 hydrogen,
 chloro,
 bromo or
 nitro;
X is
 fluoro,
 chloro or
 bromo;
Z is
 —OH,
 loweralkoxy,
 arloweralkoxy,
 —OM.

The most preferred compounds of this invention describe a class of chemical compounds which have particular usefulness as anti-inflammatory, analgesic and antipyretic agents. These compounds are described in formula III

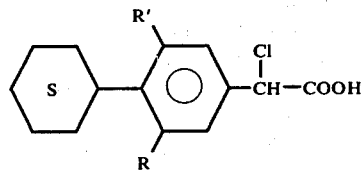

where:
R is
 hydroxyl,
 loweralkoxy,
 acetyloxy,
 acetyl, or
 loweralkyl; and
R' is
 hydrogen,
 chloro,
 bromo or
 nitro.

Included within the scope of this further special embodiment are the racemic mixtures as well as the dextro and levorotatory isomers thereof.

In the descriptive portions of this invention, the following definitions apply:

The term loweralkyl refers to a loweralkyl hydrocarbon group containing from 1 to about 6 carbon atoms which may be straight chained or branched.

The acyl radical may be any organic radical derived from an organic acid by the removal of its hydroxyl group such as formyl, acetyl, propionyl, 3-carboxypropionyl, 3-carboxy-2-propenoyl, camphoryl, benzoyl, toluoyl or heteroyl such as pyridinoyl, piperidinoyl, thenoyl, etc.

Loweralkoxy signifies an alkoxy group containing from 1 to about 6 carbon atoms which may be straight chained or branched.

The preferred alkali or alkaline earth metals are sodium, potassium, calcium and magnesium.

The term ammonium salt refers to the cation formed when ammonia or an organic amine react with the carboxyl group to form ammonium salts of the structure given in the formula. The ammonium salts are formed with a (1) loweralkylamines such as methylamine, diethylamine, triethylamine; (2) hydroxyloweralkylamines such as β-hydroxyethylamine; (3) heterocyclic amines such as 2-aminopyridine, piperazine, piperidine; (4) aralkylamines such as α-methylbenzylamine, phenethylamine; (5) cycloalkylamines such as cyclohexylamine; (6) alkaloids such as quinine, cinchonidine, cinchonine, ephedrine.

Representative compounds of this invention which are particularly useful are as follows:
 α-chloro-3-hydroxy-4-cyclohexylphenylacetic acid
 α-chloro-3-methoxy-4-cyclohexylphenylacetic acid
 α-chloro-3-acetoxy-4-cyclohexylphenylacetic acid
 α-chloro-3-methyl-4-cyclohexylphenylacetic acid The compounds of this invention may be prepared by the following general procedures. Condensation of a cycloalkylbenzene with a loweralkyl or aralkyl oxalyl chloride in the presence of anhydrous aluminum chloride results in a p-cycloalkylphenylglyoxylate. The resulting loweralkyl or aralkyl esters of the p-cycloalkylphenylglyoxylic acid may then be alkylated to obtain the corresponding loweralkyl esters of a 3-alkyl-4-cycloalkylphenylglyoxylic acid. Alkylation is carried out under Friedel Crafts conditions with an alkyl halide and aluminum chloride. The following reaction equations illustrate these methods.

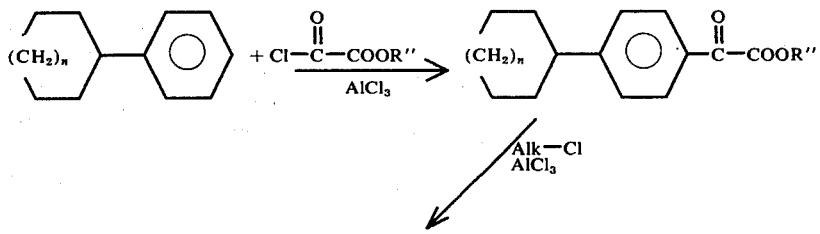

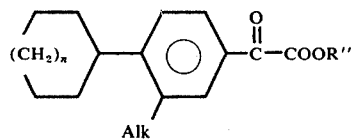

where R" is loweralkyl or arloweralkyl and Hal is chloro or bromo.

When a loweralkyl group is desired in the cycloalkyl or acylated with loweracyl chlorides or anhydrides to the acyloxy compound in the presence of a tertiary amine such as pyridine,

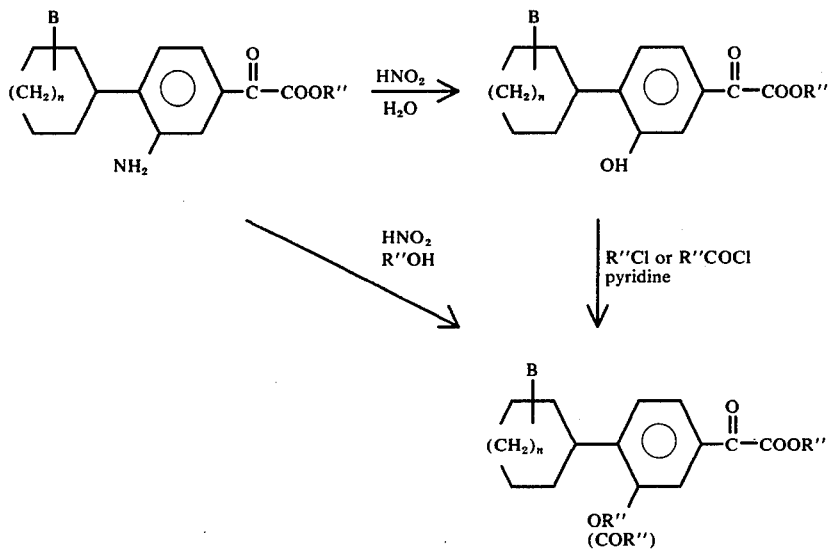

ring, then the condensation will take place with the appropriate loweralkyl benzene cycloalkyl followed by alkylation.

Nitration or halogenation with chlorine or bromine may be carried out on the 3-substituted-4-cycloalkyl-phenylglyoxylate to obtain the corresponding 3,5-

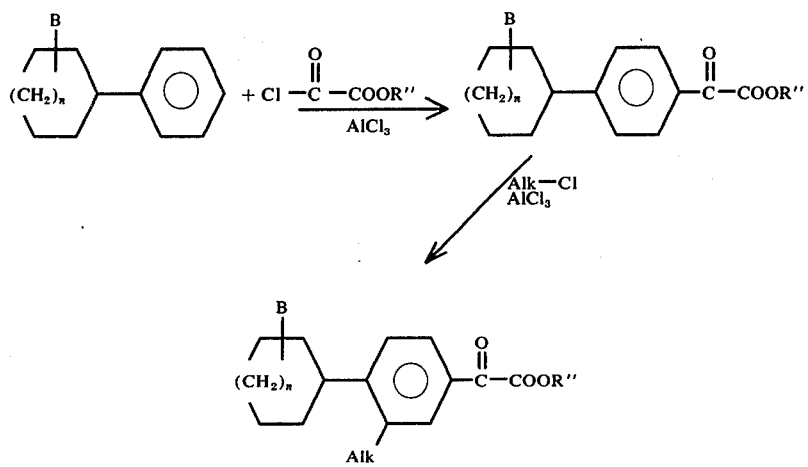

A 3-amino-4-cycloalkylphenylglyoxylate may be diazotized and heated in an aqueous medium to form the 3-hydroxy-4-cycloalkylphenylglyoxylate or heated in an alcohol to form the 3-alkoxy-4-cycloalkylphenylglyoxylate. The hydroxyl group may also be alkylated with loweralkyl halides or sulfates to the alkoxyl group disubstituted-4-cycloalkylphenylglyoxylate. This may be carried out at any appropriate stage of the synthesis in order to obtain the desired substituents. Thus, for example, a 3-alkyl compound may thus be nitrated, chlorinated or brominated to the 3-chloro, 3-bromo or 3-nitro-5-alkyl compounds.

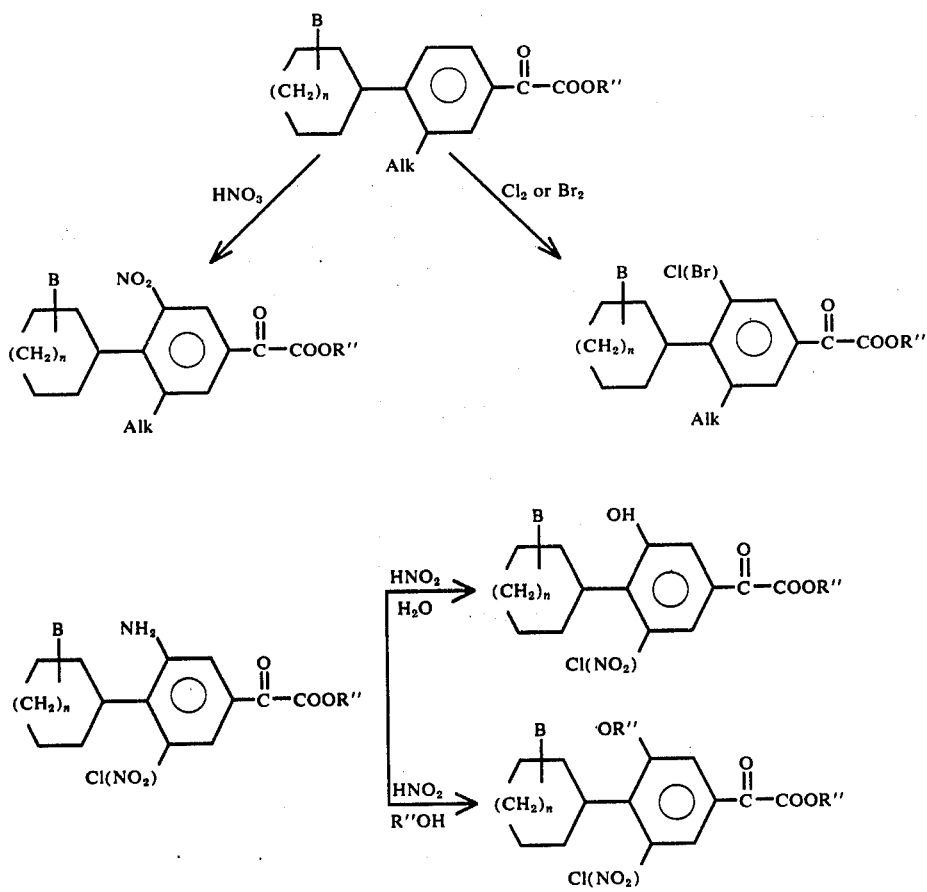

where R" is lower alkyl

The p-cycloalkylphenylglyoxylate ester is converted to the corresponding p-cycloalkylphenylglycolate ester by hydrogenation in the presence of platinum oxide. In the special case when R' is substituent sensitive to catalytic hydrogenation, e.g. when R' is NO₂, I, etc., a selective reduction of the keto function is effected with sodium borohydride to give the p-cycloalkylphenylglycolate ester.

It is often more convenient to convert one substituent to another after the reduction of the glyoxylate to the glycolate. Thus, for example, a 3-nitro-4-cycloalkylphenylglyoxylate can be reduced under sodium borohydride conditions as above to the 3-nitro-4-cycloalkylphenylglycolate. This in turn may then be catalytically reduced to the 3-amino-4-cycloalkylphenylglycolate. The amino group can then be diazotized as above to the desired substituents. This may be carried out on any of

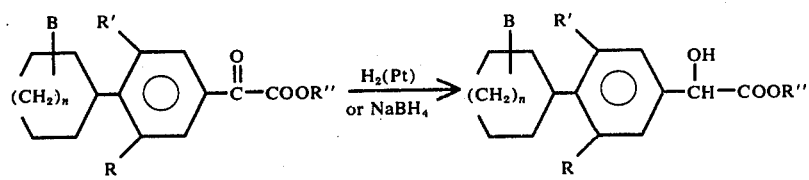

the nitro compounds as outlined. The diazotized products may then be hydrolyzed to the glycolic acid.

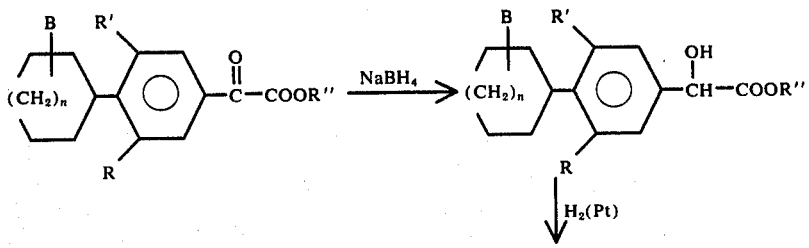

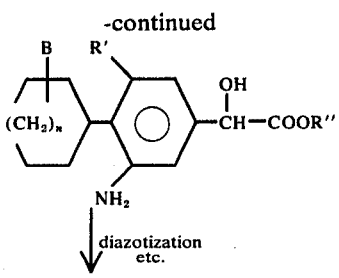

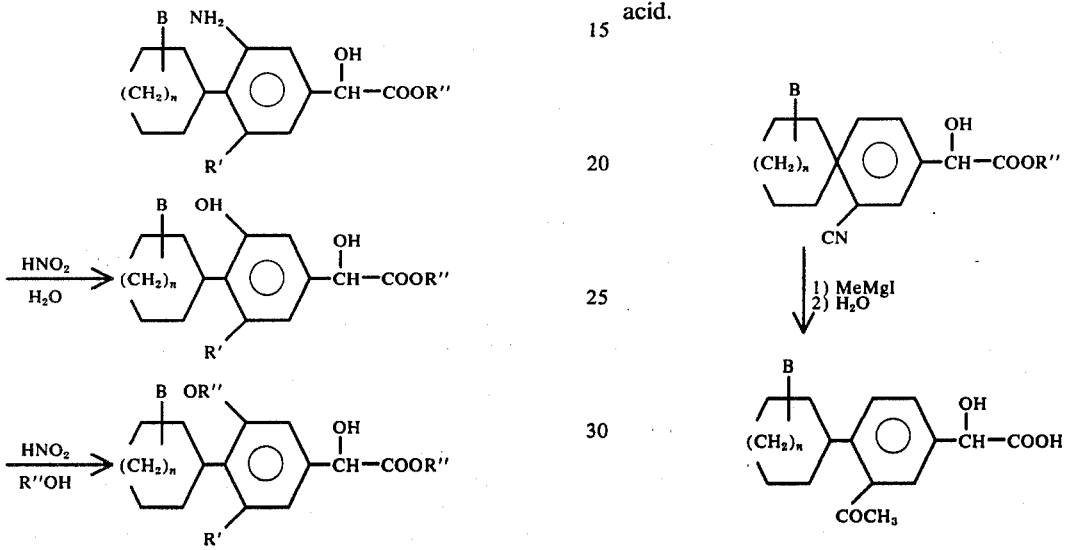

where:
R' is
 hydrogen,
 fluoro,
 chloro,
 bromo,
 trifluoromethyl,
 nitro.

The glycolate esters may be hydrolyzed to the corresponding p-cycloalkylphenylglycolic acid.

A 3-cyanoglycolate may be reacted with two equivalents of methylmagnesium iodide in tetrahydrofuran followed by hydrolysis to obtain the 3-acetylglycolic acid.

When a substituted 4-cycloalkylphenylglycolate is reacted with a phosphorus trihalide, phosphorus pentahalide, phosphorus oxyhalide, sulfurylhalide, thionyl halide, or sulfur halide the corresponding substituted α-halo-4-cycloalkylphenylacetate is prepared.

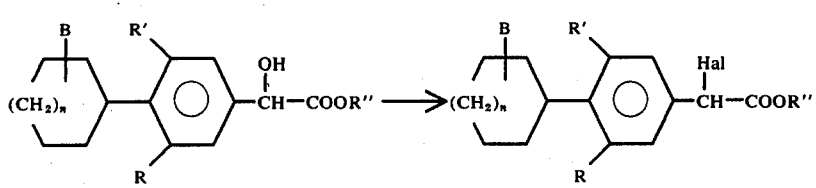

where R'' is lower alkyl;
where Hal is fluoro, chloro, bromo or iodo.

Reaction of an α-sulfonate with a metal halide (preferably an alkali halide) results in the corresponding α-halo compound.

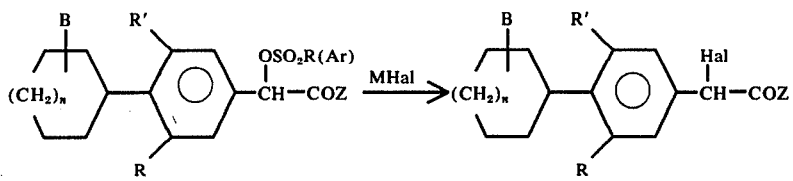

where Z is as described hereinabove.

The corresponding α-haloacetic acid may be prepared by heating the ester with acetic acid containing the corresponding hydrogen halide.

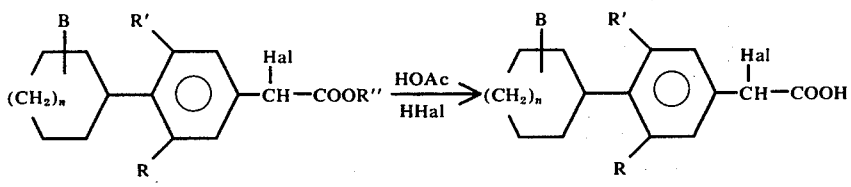

where R'' is lower alkyl.

The substituted α-fluoro-4-cycloalkylphenylacetic acid derivatives may also be obtained from the corresponding α-iodo, α-bromo or α-chloro-4-cycloalkylphenylacetic acid derivatives by reaction with potassium fluoride at about 130°–200° C.

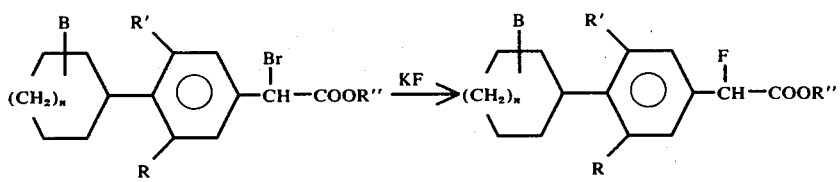

This invention further relates to the acid addition salts formed by the action of one equivalent of a suitable base with the substituted α-halo-4-cycloalkylphenylacetic acid. Suitable bases thus include for example the alkali metal alkoxides such as sodium methoxide, etc., and the alkali metal and alkaline earth metal hydroxides, carbonates, bicarbonates, etc. (such as sodium hydroxide, potassium hydroxide, calcium hydroxide, potassium carbonate, sodium bicarbonate, magnesium bicarbonate, etc.). Also, the aluminum salts of the instant products may be obtained by treating the corresponding sodium salt with an appropriate aluminum complex such as aluminum hydroxy chloride hexahydrate, etc. The ammonium salts may be made by reaction with the corresponding amine such as methylamine, diethylamine, β-hydroxyethylamine, piperazine, piperidine, α-methylbenzylamine, cyclohexylamine, triethylamine, phenethylamine, etc. The acid addition salts thus obtained are the functional equivalent of the corresponding substituted α-halo-p-cycloalkylphenylacetic acid products and one skilled in the art will appreciate that to the extent that the instant acids are useful in therapy, the variety of acid addition salts embraced by this invention are limited only by the criterion that the bases employed in forming the therapeutically useful salts be both non-toxic and physiologically acceptable. The alkaloidal salts are useful for effecting optical resolutions.

mers. These may be separated by any of the various methods of resolution. One method that may be employed is combining the racemic compound with an optically active compound by salt formtion or ester formation to form two diastereomeric products. If the instant acids are added to an optically active base, then two diastereomeric salts are produced which possess different properties and different solubilities and can be separated by fractional crystallization. When the salts have been completely separated by repeated crystallization, the base is split off by acid hydrolysis and the pure d or l acids are obtained. Preferably, a cycloalkylphenylglycolic acid is reacted in alcoholic or acetone solution with an equivalent amount of the optically active primary, secondary or tertiary amine such as cinchonidine, cinchonine, quinine, ephedrine, α-methylbenzylamine, sec-butylamine, sec-amylamine, etc. The diastereomeric amine salts produced thereby are separated by fractional crystallization and each optically active salt is hydrolyzed with dilute mineral acid to produce the dextro or levo form of the p-cycloalkylphenylglycolic acid.

Still alternatively, a p-cycloalkylphenylglycolate may be reacted with an optically active alcohol such as l-menthol or d-borneol, or l-α-methylbenzylalcohol, to produce a mixture of diastereomeric p-cycloalkylphenylglycolate esters which may be separated by fractional crystallization. Each optically active ester may be hydrolyzed with mineral acid or alkali to its respective optically active acid. The optically active acids can also be recovered from the α-methylbenzyl esters by hydrogenolysis in the presence of palladium.

The optically active glycolate may then be reacted with a phosphorus trihalide, phosphorus pentahalide,

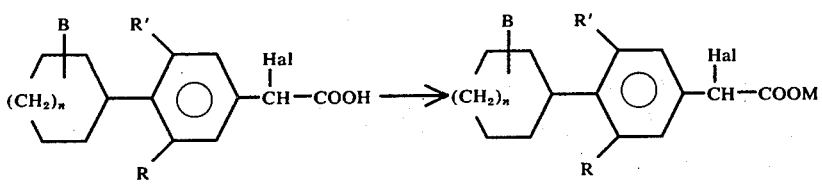

These and other equivalent methods for the preparation of the acids, esters, and derivatives of the instant products will be apparent to those having ordinary skill in the art.

The products of this invention may be obtained as racemic mixtures of their dextro and levorotatory isophosphorus oxyhalide, sulfurylhalide, thionylhalide or sulfur halide to give an optically active α-halo p-cycloalkylphenylacetic acid or ester thereof.

The racemic chloroacetic acids or esters may also be resolved into their optical isomers by the processes described for the glycolic acids or esters.

More detailed data regarding the anti-inflammatory activity of the claimed compounds, their administration and dosage unit forms, and pharmacological tests carried out to prove their effectiveness are described in U.S. Pat. No. 3,852,323 which is included by reference herein.

The following are detailed examples which show the preparation of the compounds of this invention. They are to be construed as illustrations of said compounds and are not intended to be limitations thereof.

EXAMPLE 1

Ethyl α,3-dichloro-4-cyclohexylphenylacetate

A mixture of 221.75 g. (0.747 mole) of ethyl 3-chloro-4-cyclohexylphenylglycolate prepared as described in U.S. Pat. No. 3,852,323 is stirred with 106.67 g. (0.895 mole) of thionyl chloride at room temperature for 24 hours and then heated to reflux for 6 hours. The cold reaction mixture is poured into 1125 ml. of ice-cold water with stirring. The mixture is extracted with 800 ml. of ether. The ethereal solution is washed with 450 ml. of cold saturated sodium hydrocarbonate solution followed by washing twice, each time with 250 ml. of cold water. The ethereal solution is dried over anhydrous sodium sulfate and filtered. The solvent is removed in vacuo to obtain ethyl α,3-dichloro-4-cyclohexylphenylacetate.

EXAMPLE 2

When the procedures of Example 1 is followed but ethyl 3-chloro-4-cyclohexylphenylglycolate is replaced by the dl, d and l glycolates of this invention, then the corresponding dl, d and l α-chloroacetate products are prepared. A representative list of the compounds obtained are shown in Table I, below.

TABLE I ethyl α-chloro-3-hydroxy-4-cyclohexylphenylacetate
ethyl α-chloro-3-methoxy-4-cyclohexylphenylacetate
ethyl α-chloro-3-acetyl-4-cyclohexylphenylacetate
ethyl α-chloro-3-methyl-4-cyclohexylphenylacetate
ethyl α-chloro-3-nitro-5-methyl-4-cyclohexylphenylacetate
ethyl α,3-dichloro-5-methyl-4-cyclohexylphenylacetate
ethyl α,3-dichloro-5-methoxy-4-cyclohexylphenylacetate
ethyl α,3-dichloro-5-methyl-4-cyclohexylphenylacetate
ethyl α-chloro-3-methyl-5-fluoro-4-cyclohexylphenylacetate
ethyl α-chloro-3-methyl-5-bromo-4-cyclohexylphenylacetate
ethyl α-chloro-3-methyl-5-trifluoromethyl-4-cyclohexylphenylacetate
ethyl α,3-dichloro-5-acetyl-4-cyclohexylphenylacetate
ethyl α-chloro-3-methyl-5-nitro-4-cyclohexylphenylacetate
ethyl α-chloro-3-acetyl-5-fluoro-4-cyclohexylphenylacetate
ethyl α-chloro-3-acetyl-5-bromo-4-cyclohexylphenylacetate
ethyl α-chloro-3-hydroxy-5-trifluoromethyl-4-cyclohexylphenylacetate
ethyl α-chloro-3-acetyl-5-trifluoromethyl-4-cyclohexylphenylacetate
ethyl α-chloro-3-methoxy-5-nitro-4-cyclohexylphenylacetate
ethyl α-chloro-3-acetyloxy-5-nitro-4-cyclohexylphenylacetate

EXAMPLE 3

α,3-Dichloro-4-cyclohexylphenylacetic acid

A mixture of 52.5 g. (0.167 moles) of the ethyl α,3-dichloro-4-cyclohexylphenylacetate and 160 ml. of glacial acetic acid containing 40 ml. of 37% hydrochloric acid is refluxed for 20 hours. The mixture is concentrated under reduced pressure to give a gummy residue. The latter material is dissolved in 300 ml. of n-hexane, washed with ice-cold water (100 ml. total), dried over sodium sulfate and filtered. The hexane is removed to give α,3-dichloro-4-cyclohexylphenylacetic acid.

EXAMPLE 4

When the procedures of Example 3 is followed but ethyl α,3-dichloro-4-cyclohexylphenylacetate is replaced by the dl, d and l α-chloroacetates of this invention, then the corresponding dl, d and l α-chloroacetic acids are prepared. A representative list of the products obtained are shown in Table I, below.

TABLE I

α-chloro-3-hydroxy-4-cyclohexylphenylacetic acid
α-chloro-3-methoxy-4-cyclohexylphenylacetic acid
α-chloro-3-acetyl-4-cyclohexylphenylacetic acid
α-chloro-3-methyl-4-cyclohexylphenylacetic acid
α-chloro-3-nitro-5-methyl-4-cyclohexylphenylacetic acid
α,3-dichloro-5-methyl-4-cyclohexylphenylacetic acid
α,3-dichloro-5-methoxy-4-cyclohexylphenylacetic acid
α,3-dichloro-5-methyl-4-cyclohexylphenylacetic acid
α-chloro-3-methyl-5-fluoro-4-cyclohexylphenylacetic acid
α-chloro-3-methyl-5-bromo-4-cyclohexylphenylacetic acid
α-chloro-3-methyl-5-trifluoromethyl-4-cyclohexylphenylacetic acid
α,3-dichloro-5-acetyl-4-cyclohexylphenylacetic acid
α-chloro-3-methyl-5-nitro-4-cyclohexylphenylacetic acid
α-chloro-3-acetyl-5-fluoro-4-cyclohexylphenylacetic acid
α-chloro-3-acetyl-5-bromo-4-cyclohexylphenylacetic acid
α-chloro-3-hydroxy-5-trifluoromethyl-4-cyclohexylphenylacetic acid
α-chloro-3-acetyl-5-trifluoromethyl-4-cyclohexylphenylacetic acid
α-chloro-3-methoxy-5-nitro-4-cyclohexylphenylacetic acid
α-chloro-3-acetyloxy-5-nitro-4-cyclohexylphenylacetic acid
α-chloro-3-iodo-5-acetyl-4-cyclohexylphenylacetic acid

EXAMPLE 5

α,3-Dichloro-4-cyclohexylphenylacetic acid, sodium salt

A solution of 12.4 g. of sodium bicarbonate in 135 ml. water is added dropwise to a stirred solution of 47.1 g. (0.164 moles) of α,3-dichloro-4-cyclohexylphenylacetic acid in 150 cc. of methanol. The solvent is removed in vacuo and the residue is dried by repeated distillations with anhydrous ethanol. The crystalline residue is triturated with ether (100 cc.), collected on a filter, and washed with ether. Drying in a vacuum desiccator affords α,3-dichloro-4-cyclohexylphenylacetic acid, sodium salt.

When an equimolar amount of sodium bicarbonate in the above reaction is replaced by the compounds of Table I below, then the corresponding salt of Table II below is prepared.

TABLE I sodium hydroxide
potassium hydroxide
calcium hydroxide
potassium carbonate
magnesium bicarbonate

TABLE II

α,3-dichloro-4-cyclohexylphenylacetic acid, sodium salt
α,3-dichloro-4-cyclohexylphenylacetic acid, potassium salt
α,3-dichloro-4-cyclohexylphenylacetic acid, calcium salt
α,3-dichloro-4-cyclohexylphenylacetic acid, magnesium salt When α,3-dichloro-4-cyclohexylphenylacetic acid is replaced by d α,3-dichloro-4-cyclohexylphenylacetic acid and l α,3-dichloro-4-cyclohexylphenylacetic acid then the products prepared are:
  d α,3-dichloro-4-cyclohexylphenylacetic acid, sodium salt
  d α,3-dichloro-4-cyclohexylphenylacetic acid, potassium salt
  d α,3-dichloro-4-cyclohexylphenylacetic acid, calcium salt
  d α,3-dichloro-4-cyclohexylphenylacetic acid, magnesium salt
  l α,3-dichloro-4-cyclohexylphenylacetic acid, sodium salt
  l α,3-dichloro-4-cyclohexylphenylacetic acid, potassium salt
  l α,3-dichloro-4-cyclohexylphenylacetic acid, calcium salt
  l α,3-dichloro-4-cyclohexylphenylacetic acid, magnesium salt When the dl, d and l α-chloroacetic acid compounds of the Tables given hereinabove are used in the above reaction, the corresponding salt is prepared.

EXAMPLE 5a

α,3-Dichloro-4-cyclohexylphenylacetic acid, diethylammonium salt

Anhydrous diethylamine (0.11 moles) is added dropwise to a stirred solution of α,3-dichloro-4-cyclohexylphenylacetic acid (0.10 moles) in 100 ml. of n-hexane at 0° C. The precipitate is collected on a filter, washed with n-hexane, and dried in a vacuum desiccator to obtain α,3-dichloro-4-cyclohexylphenylacetic acid, diethylammonium salt.

When diethylamine in the above reaction is replaced by an equimolar amount of the compounds of Table I, below, then the corresponding product of Table II, below is prepared.

TABLE I dimethylamine
β-hydroxyethylamine
piperazine
piperidine
α-methylbenzylamine
cyclohexylamine
triethylamine
phenethylamine

TABLE II

α,3-dichloro-4-cyclohexylphenylacetic acid, dimethylammonium salt
α,3-dichloro-4-cyclohexylphenylacetic acid, β-hydroxyethylammonium salt
α,3-dichloro-4-cyclohexylphenylacetic acid, piperazinium salt
α,3-dichloro-4-cyclohexylphenylacetic acid, piperidinium salt
α,3-dichloro-4-cyclohexylphenylacetic acid, α-methylbenzylammonium salt
α,3-dichloro-4-cyclohexylphenylacetic acid, cyclohexylammonium salt
α,3-dichloro-4-cyclohexylphenylacetic acid, triethylammonium salt
α,3-dichloro-4-cyclohexylphenylacetic acid, phenethylammonium salt Likewise the corresponding ammonium salts of the compounds according to the present invention as given in the Tables hereinabove are produced in the same manner.

EXAMPLE 6

Ethyl α-bromo-3-chloro-4-cyclohexylphenylacetate

To 15.0 g. (0.0476 moles) of ethyl 3-chloro-4-cyclohexylphenylglycolate there is added slowly with stirring at 40°–50° C 23 g. (0.053 moles) of phosphorus pentabromide. The mixture is stirred at room temperature for 16 hours, then diluted with 70 ml. of petroleum ether, and poured into 125 ml. of ice-cold water. The organic phase is separated, washed with saturated aqueous sodium hydrogen carbonate solution, dried over anhydrous sodium sulfate, filtered and the solvent removed in vacuo to obtain ethyl α-bromo-3-chloro-4-cyclohexylphenylacetate.

When ethyl 3-chloro-4-cyclohexylphenylglycolate in the above procedure is replaced by d ethyl 3-chloro-4-cyclohexylphenylglycolate, l ethyl 3-chloro-4-cyclohexylphenylglycolate, then the products prepared are d ethyl α-bromo-3-chloro-4-cyclohexylphenylglycolate or l ethyl α-bromo-3-chloro-4-cyclohexylphenylglycolate.

When the above procedure is followed using the various glycolates of this invention, then the corresponding α-bromoacetates are prepared.

EXAMPLE 7

When the α-bromoacetates of Example 6 are hydrolyzed according to the procedures of Examples 3 and 4, then the corresponding dl, d and l α-bromo-3-chloro-4- cyclohexylphenylacetic acid compounds and the various α-bromoacetic acids are prepared.

EXAMPLE 8

When the α-bromoacetic acid compounds are reacted according to the procedures of Example 5, then the corresponding α-bromoacetic acid salts are prepared.

EXAMPLE 9

Ethyl α-fluoro-3-chloro-4-cyclohexylphenylacetate

A mixture of 118 g. (0.33 moles) of ethyl α-bromo-3-chloro-4-cyclohexylphenylacetate is vigorously stirred at 130°–140° C with 29 g. (0.5 moles) of potassium fluoride in 100 ml. of ethylene glycol for 12 hours. The reaction mixture is cooled and 400 ml. of water is added and the crude product separates. The aqueous glycol mixture is extracted with ether, the ether is then dried, evaporated to dryness and upon distillation results in ethyl α-fluoro-3-chloro-4-cyclohexylphenylacetate.

When the above procedure is followed using the various α-bromoacetates of this invention, then the corresponding α-fluoroacetates are prepared.

EXAMPLE 10

When the α-fluoroacetates of Example 9 are hydrolyzed according to the procedures of Examples 3 and 4, then the corresponding α-fluoro-3-chloro-4-cyclohexylphenylacetic acid compound and the various α-fluoroacetic acids are prepared.

EXAMPLE 11

When the α-fluoroacetic acid compounds are reacted according to the procedures of Example 5, then the corresponding α-fluoroacetic acid salts are prepared.

EXAMPLE 12

Ethyl α-iodo-3-chloro-4-cyclohexylphenylacetate

A mixture of 40.5 g. (0.1 moles) of ethyl α-bromo-3-chloro-4-cyclohexylphenylacetate and 150 g. of sodium iodide in 1 liter of anhydrous acetone is refluxed for 4 hours. The reaction mixture is then evaporated to dryness and extracted with ether. The ether is then washed with water, dried and evaporated to dryness to obtain ethyl α-iodo-3-chloro-4-cyclohexylphenylacetate.

When the above procedure is followed using the various α-bromoacetates of this invention then the corresponding α-iodoacetates are prepared.

EXAMPLE 13

When the α-iodoacetates of Example 12 are hydrolyzed according to the procedures of Examples 3 and 4, then the corresponding α-iodo-3-chloro-4-cyclohexylphenylacetic acid compound and the various α-iodoacetic acids are prepared.

EXAMPLE 14

When the α-iodoacetic acid compounds are reacted according to the procedures of Example 5, then the corresponding α-iodoacetic acid salts are prepared.

The preparation of the intermediates useful for making the compounds according to the present invention is described more in detail in U.S. Pat. Nos. 3,864,384 and 3,852,323 which patents are included herein by reference.

We claim:

1. A compound of the formula

[Structure: $(CH_2)_n$ cyclohexyl ring with B substituent, connected to phenyl ring bearing R' and R substituents, with —CH(X)—COZ group]

where:
n is
  0–2;
B is
  hydrogen or
  loweralkyl;
R is
  hydroxy,
  loweralkoxy,
  acetyloxy,
  acetyl or
  loweralkyl;
R' is
  hydrogen,
  fluoro,
  chloro,
  bromo,
  trifluoromethyl or
  nitro;
X is
  halo;
Z is
  —OH,
  loweralkoxy,
  arloweralkoxy, or
  —OM where M is an alkali, alkaline earth or aluminum metal or an ammonium salt.

2. A compound according to claim 1 which is dextrorotatory.

3. A compound according to claim 1 which is levorotatory.

4. A compound according to claim 1 of the formula

[Structure: thiophene (S) ring connected to phenyl ring bearing R' and R substituents, with —CH(X)—COZ group]

5. α-chloro-3-methyl-4-cyclohexylphenylacetic acid.
6. α-chloro-3-acetyl-4-cyclohexylphenylacetic acid.
7. α-chloro-3-methoxy-4-cyclohexylphenylacetic acid.
8. α-chloro-3-hydroxy-4-cyclohexylphenylacetic acid.
9. α-chloro-3-acetyloxy-4-cyclohexylphenylacetic acid.

* * * * *